(12) United States Patent
Anderson, Jr. et al.

(10) Patent No.: US 6,235,197 B1
(45) Date of Patent: *May 22, 2001

(54) ELECTROCHEMICALLY REGENERATED ION NEUTRALIZATION AND CONCENTRATION DEVICES AND SYSTEMS

(75) Inventors: James M. Anderson, Jr., Arlington Heights; Raaidah Saari-Nordhaus, Lindenhurst, both of IL (US); Carl W. Sims, St. Paul; Yuri E. Gerner, Mendota Heights, both of MN (US)

(73) Assignee: Alltech Associates, Inc., Deerfield, IL (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/298,440

(22) Filed: Apr. 23, 1999

Related U.S. Application Data

(63) Continuation of application No. 08/818,064, filed on Mar. 14, 1997, now Pat. No. 5,935,443, which is a continuation-in-part of application No. 08/609,171, filed on Mar. 1, 1996, now Pat. No. 6,093,327, which is a continuation-in-part of application No. 08/486,210, filed on Jun. 7, 1995, now abandoned, which is a continuation-in-part of application No. 08/399,706, filed on Mar. 3, 1995, now abandoned.

(51) Int. Cl.$^7$ .................................................... B01D 15/08
(52) U.S. Cl. .................... 210/635; 210/638; 210/656; 210/659; 210/198.2; 73/61.55; 436/161
(58) Field of Search ................................ 210/635, 638, 210/656, 659, 660, 670, 675, 748, 198.2, 243; 436/161; 73/61.52, 61.53, 61.58, 61.55; 204/533

(56) References Cited

U.S. PATENT DOCUMENTS

| 2,980,598 | 4/1961 | Stoddard | 204/151 |
| 3,557,532 | 1/1971 | Broerman | 210/656 |

(List continued on next page.)

FOREIGN PATENT DOCUMENTS

| 52-31958 | 3/1977 | (JP) | 210/198.2 |
| 53-116278 | 11/1978 | (JP) | 210/198.2 |
| 60-207055 | 3/1984 | (JP) | 210/198.2 |
| 59-133459 | 7/1984 | (JP) | 210/198.2 |

OTHER PUBLICATIONS

G.I. Mal'tsev et al., "Investigation of Ion Exchange on KU–2 Cationite on Application of an Audio–Frequency Alternating Electrical Field", 3 pages (1971).

(List continued on next page.)

*Primary Examiner*—Ernest G. Therkorn
(74) *Attorney, Agent, or Firm*—Brinks Hofer Gilson & Lione

(57) ABSTRACT

A system and method for electrochemically regenerated ion neutralization and concentration is disclosed. In one aspect of the invention, a system is provided comprising a HPLC column pump, a concentrator column, an analytical column, a suppressor, a detector, a mixed bed deionizing resin, a sample injector, and a neutralization cartridge.

4 Claims, 3 Drawing Sheets

U.S. PATENT DOCUMENTS

| | | | |
|---|---|---|---|
| 3,594,294 | 7/1971 | Pretorius et al. | 210/656 |
| 3,640,813 | 2/1972 | Nerenberg | 204/615 |
| 3,694,335 | 9/1972 | Pretorius et al. | 204/615 |
| 3,722,181 | 3/1973 | Kirkland et al. | 95/88 |
| 3,795,313 | 3/1974 | Kirkland et al. | 210/198.2 |
| 3,897,213 | 7/1975 | Stevens et al. | 422/81 |
| 3,918,906 | 11/1975 | Small et al. | 436/161 |
| 3,920,397 | 11/1975 | Small et al. | 436/79 |
| 3,925,019 | 12/1975 | Hamish et al. | 436/79 |
| 3,926,559 | 12/1975 | Stevens | 436/79 |
| 4,242,097 | 12/1980 | Rich, Jr. et al. | 436/100 |
| 4,265,634 | 5/1981 | Pohl | 436/161 |
| 4,314,823 | 2/1982 | Rich, Jr. et al. | 436/100 |
| 4,403,039 | 9/1983 | Ban et al. | 436/150 |
| 4,455,233 | 6/1984 | Pohl et al. | 210/635 |
| 4,459,357 | 7/1984 | Jansen et al. | 204/520 |
| 4,474,664 | 10/1984 | Stevens et al. | 210/656 |
| 4,486,312 | 12/1984 | Slingsby et al. | 210/656 |
| 4,584,075 | 4/1986 | Goldstein et al. | 204/522 |
| 4,594,135 | 6/1986 | Goldstein | 204/551 |
| 4,632,745 | 12/1986 | Giuffrida et al. | 204/632 |
| 4,643,814 | 2/1987 | Goldstein | 204/551 |
| 4,672,042 | 6/1987 | Ross, Jr. et al. | 436/161 |
| 4,732,686 | 3/1988 | Small et al. | 210/656 |
| 4,747,929 | 5/1988 | Siu et al. | 204/632 |
| 4,751,004 | 6/1988 | Stevens et al. | 210/659 |
| 4,751,189 | 6/1988 | Rocklin | 436/150 |
| 4,759,405 | 7/1988 | Metzger | 165/173 |
| 4,861,555 | 8/1989 | Mowery, Jr. | 422/70 |
| 4,925,541 | 5/1990 | Giuffrida et al. | 204/524 |
| 4,952,126 | 8/1990 | Hanaoka et al. | 422/70 |
| 4,981,804 | 1/1991 | Hanaoka et al. | 436/150 |
| 4,999,098 | 3/1991 | Pohl et al. | 210/670 |
| 5,032,265 | 7/1991 | Jha et al. | 210/195.2 |
| 5,045,204 | 9/1991 | Dasgupta et al. | 210/635 |
| 5,062,961 | 11/1991 | Doury-Berthod et al. | 210/656 |
| 5,068,090 | 11/1991 | Connolly | 422/82.02 |
| 5,132,018 | 7/1992 | Jones et al. | 210/656 |
| 5,149,661 | 9/1992 | Gjerde et al. | 436/178 |
| 5,248,426 | 9/1993 | Stillian et al. | 210/635 |
| 5,352,360 | 10/1994 | Stillian et al. | 210/198.2 |
| 5,419,819 | 5/1995 | Park | 204/157.2 |
| 5,423,965 | 6/1995 | Kunz | 205/702 |
| 5,518,622 * | 5/1996 | Stillian | 210/198.2 |
| 5,597,481 * | 1/1997 | Stillian | 210/198.2 |
| 5,597,734 | 1/1997 | Small et al. | 436/161 |
| 5,633,171 | 5/1997 | Small et al. | 436/161 |
| 5,759,405 * | 6/1998 | Anderson | 210/198.2 |
| 5,914,025 | 6/1999 | Small | 205/789 |
| 5,935,443 * | 8/1999 | Anderson | 210/198.2 |

OTHER PUBLICATIONS

Z. W. Tian et al., "High–Performance Electrochemical Suppressor For Ion Chromatography", *Journal of Chromatography*, vol. 439, pp. 159–163 (1988).

D.L. Strong et al., "Electrodialytic Membrane Suppressor for Ion Chromatography", *Analytical Chemistry*, vol. 61, pp. 939–945 (1989).

D. T. Gjerde et al., "Suspension Postcolumn Reaction Detection Method for Liquid Chromatography", *Analytical Chemistry*, vol. 62, pp. 612–614 (1990).

A. Henshall et al., A Recent Development in Ion Chromatography Detection: "The Self–Regenerating Suppressor" (1992).

Brochure of Applicants' assignee entitled "Improve the Performance of Any Ion Chromatograph", 4 pages, Bulletin #284, Alltech Associated, Inc. (1993).

S. Rabin et al., "New Membrane–Based Electrolytic Suppressor Device for Suppressed Conductivity Detection in Ion Chromatography", *Journal of Chromatography*, vol. 640, pp. 97–109 (1993).

R. S. Nordhaus et al., "Ion Chromatographic Analysis of Anions Using a Solid–Phase Chemical Suppressor", 9 pages, Reprinted from *American Laboratory* (1994).

Brochure entitled "Microparticulate Chemical Suppression With Sarasep Micro Ion Chromatography", 1 page.

Brochure of Dionex™ entitled "Self–Regenerating Suppressor (SRS)".

Nafion™ Coats for Electrodes in Liquid Feed Fuel Cells.

Documents Relating to Presentation Given by Raaidah Saari–Nordhaus and James M. Anderson, Jr. on Jan. 24, 1996 in Caracus, Venezuela.

"Ion Chromatography", Hamish Small, Plenum Press.

* cited by examiner

ELECTROCHEMICALLY REGENERATED ION NEUTRALIZATION AND CONCENTRATION DEVICES AND SYSTEMS

This application is a continuation of application Ser. No. 08/818,064, filed Mar. 14, 1997, now U.S. Pat. No. 5,935,443 which is a continuation-in-part application of, and claims priority to, U.S. patent application Ser. No. 08/609,171, filed Mar. 1, 1996, now U.S. Pat. No. 6,093,327 which is a continuation-in-part application of U.S. patent application Ser. No. 08/486,210, filed Jun. 7, 1995, now abandoned which is a continuation-in-part application, and claims priority to, U.S. patent application Ser. No. 08/399,706 filed Mar. 3, 1995, now abandoned. The disclosure of application Ser. Nos. 08/609,171; 08/486,210; and 08/399,406, and the associated appendices, are incorporated by reference herein. Ser. No. 08/609,171 is attached hereto as an appendix for the convenience of the Examiner and the public.

FIELD OF THE INVENTION

This invention concerns the field of ion chromatography (IC) and, more particularly, the field of high pressure liquid chromatography (HPLC).

BACKGROUND OF THE INVENTION

The determination of inorganic constituents in concentrated acids and bases is important in a variety of chemical and other processes. However, when using ion chromatography (IC) it is often difficult to detect trace amounts of anions in concentrated bases or trace amounts of cations in concentrated acids. In other words, anion samples that are highly basic (high concentration of hydroxide) or cation samples that are highly acidic (high concentration of hydronium ions) are difficult to analyze by IC because the high concentration of hydroxide or hydronium ions mask the ion peaks (either anion or cation, respectively) of interest.

In order to address this problem, one method used in the art is to pretreat the sample using an ion resin or ion exchange bed to remove the interfering ions (e.g., the hydroxide ions in anion analysis and hydronium ions in cation analysis) from the sample. Accordingly, the interfering hydroxide or hydroniun ions may be removed by passing the sample through an ion-exchange bed or ion exchange resin which removes the interfering ions according to the following neutralization reaction:

For anion analysis, the sample is passed through a cation exchange resin in the hydronium form (X=sample anion, M=sample/hydroxide countercation):

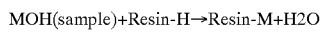

Excess sample hydroxide is neutralized to water. Sample anions are converted to their corresponding acids:

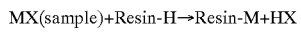

For cation analysis, the sample is passed through an anion-exchange resin in the hydroxide form (X=sample/acid counteranion, M=sample cation).

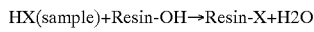

Excess sample acid is neutralized to water. Sample cations are converted to their corresponding hydroxide salts:

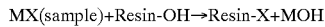

One prior art method for accomplishing the above described neutralization of interfering ions is passing the sample through a disposable pre-treatment, ion-exchange bed before flowing the sample ions to the analytical column. One such disposable ion-exchange bed known in the art is sold by the assignee of this application, ALLTECH ASSOCIATES, Inc. This pre-treatment neutralization column is sold by ALLTECH under the name ALLTECH's Maxi-Clean™ IC-OH or IC-H cartridges. These ALLTECH devices are solid-phase extraction devices used to eliminate interfering ions (e.g. matrix interferences) from samples prior to analysis by ion chromatography. The foregoing ALLTECH devices, as well as the other similar neutralization columns or cartridges presently on the market, suffer from the following drawbacks:

1) Each cartridge is normally used only once and then discarded. This can be expensive.
2) Passing the samples through the cartridges is a manual, labor intensive process that can be difficult to automate.

There have been attempts by others to address the problems of the disposable neutralization columns described above. One such method is disclosed by Siriraks and Stillian (Journal of Chromatography, 640 (1993) 151–160). Sirirak et al. disclose an electrolytically regenerated micromembrane-based technique for removing matrix interferences and neutralizing samples. According to this technique, a self-regenerating suppressor (SRS) device, which is a suppressor for reducing background noise of the mobile phase after the analytical column, is also disclosed for use as a pre-treatment (e.g., before flowing the sample to the analytical column) device for neutralization of the sample. The SRS devise is thus disclosed as a pretreatment device for trace anion determination in concentrated bases and trace cation analysis in concentrated acids.

The technique disclosed by Sirirak et al. avoids some of the prior art problems such as, for example, the need for disposing of the pretreatment cartridge after every run. The SRS device is self-regenerating. For a more detailed discussion of the SRS system, those skilled in the art are referred to the above cited Sirirak et al. article.

Despite these improvements, the SRS device is, however, not without its shortcomings. The SRS device uses sensitive membranes. These membranes have inherently low ion-exchange capacity, compared to ion-exchange resin beds, and require a complex recycling/monitoring scheme to completely neutralize strongly acidic or basic samples. Additionally, membrane-based suppressors are inherently fragile and are susceptible to rupturing under the high-pressures present ahead of the column in an IC system. Consequently, additional valves are required to neutralize the sample off-line and then insert it into the analysis stream. A separate stream of high-purity water is also required to feed the electrolytic micromembrane suppressor (the SRS) during regeneration, adding further expense and complication to the device. The present invention is intended to address the foregoing problems in the art relating to sample neutralization.

Another pre-treatment method known in the art is pre-concentrating relatively dilute samples for better detection and quantification. Many samples contain trace amounts of anions and cations at levels too low to detect by direct injection into an IC system, even where interfering ions (hydroxide and hydronium) are not present. In these situations, samples are normally pumped onto a short ion-exchange column (the pre-concentration column), which traps the sample ions of interest while the balance of the sample is flowed to waste. The trapped sample ions are then eluted from the pre-concentration column in a much smaller volume and, thus, at a correspondingly much greater concentration than in the original sample. The highly concentrated sample is then flowed to an analytical column for separation and then to a detector for detection and quantification.

In prior art pre-concentration systems, the pre-concentration column is usually installed onto a six-port sample injection valve and the sample is delivered to the preconcentration column by a separate pump. Thus, this system requires an additional pump in the IC system and can also be difficult to automate.

The present invention is also intended to address these problems as well.

SUMMARY OF THE INVENTION

A method of ion chromatography is provided using mobile phase neutralization. A mobile phase comprising interfering ions and sample ions are flowed through a neutralizer ion exchange resin thereby partially exhausting the resin and generating a neutralizer effluent comprising the sample ions. The phrase "interfering ions" refers to ions that interfere with the detection of sample ions. The neutralizer effluent is flowed to an analytical column where the sample ions are separated. The separated sample ions are then detected at a detector. The partially exhausted neutralizer ion exchange resin is regenerated by applying an electrical potential across the resin while flowing an aqueous liquid stream therethrough.

Also provided is a system for electrochemically regenerated ion neutralization for use in ion chromatography. The system preferably comprises a HPLC pump, a concentrator column, an analytical column, a suppressor, a detector, a mixed-bed dionizing resin, a sample injection valve, a sample loop, a neutralization ion exchange cartridge wherein the suppressor and neutralization ion exchange cartridge each comprises ion exchange resin and a pair of electrodes capable of applying an electrical potential across the ion exchange resin.

Further provided is a system for electrochemically regenerated ion concentration for use in ion chromatography. This system preferably comprises a HPLC pump, a concentrator column, an analytical column, a suppressor, a detector, a mixed-bed dionizing resin, a sample injection valve, a sample loop, a neutralization ion exchange cartridge wherein the suppressor and neutralization ion exchange cartridge each comprises ion exchange resin and a pair of electrodes capable of applying an electrical potential across the ion exchange resin.

DETAILED DESCRIPTION OF THE PRESENTLY PREFERRED EMBODIMENTS

Figure 1:
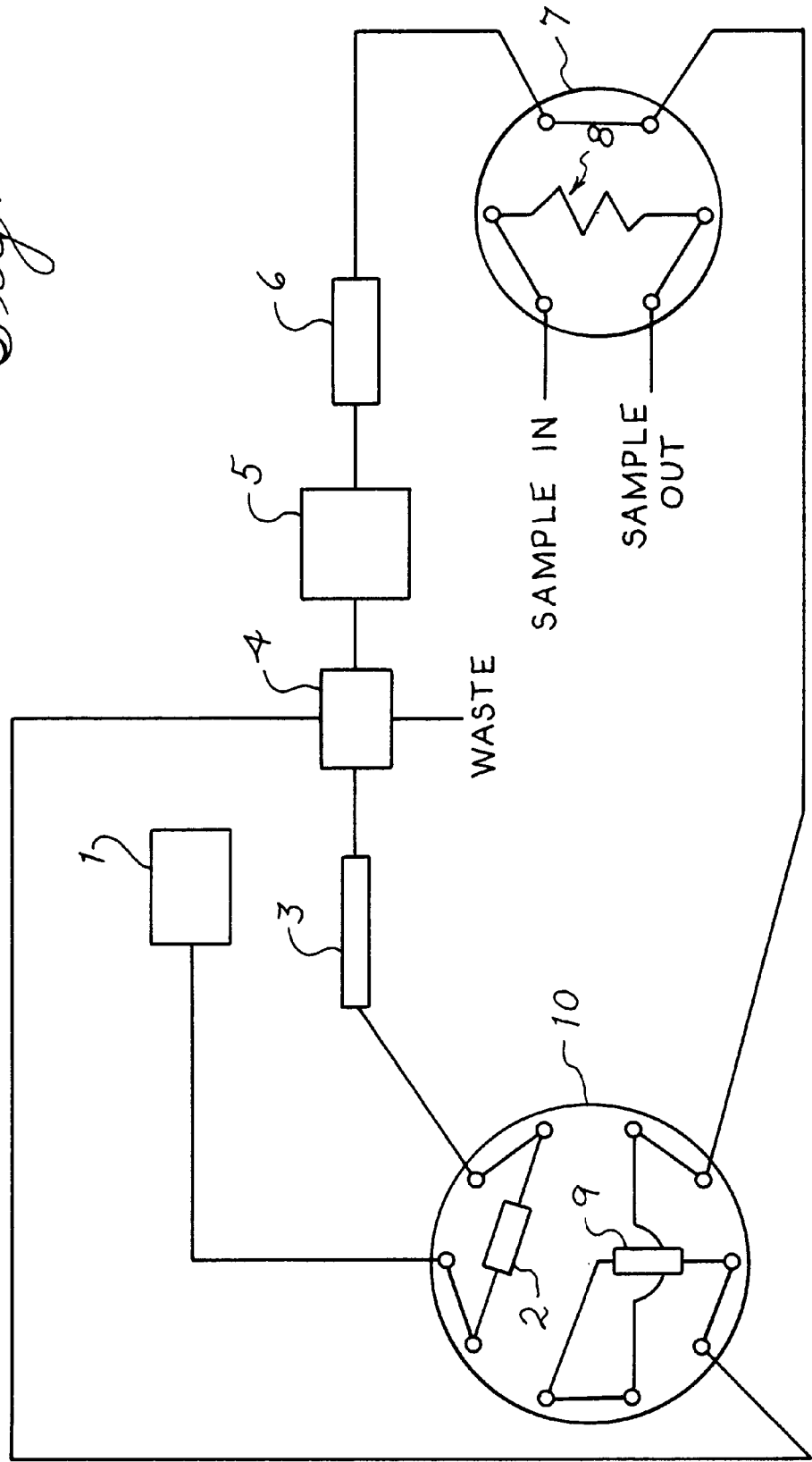
FIG. 1 is a schematic view of one aspect of the present invention showing the system configuration for sample loading in electronically regenerated ion neutralization.

In co-pending application Ser. Nos. 08/609,171; 081486, 210; and 08/399,706; the disclosures of which are all incorporated herein by reference, self-regenerating columns are disclosed which are preferably adaptable for use in the apparatus and systems of this invention. These self-regenerating columns or cartridges disclosed in the co-pending applications are preferably packed with either cation or anion exchange resin and used as the neutralization column or cartridge in the electronically regenerated ion neutralization system of the present invention. These same self-regenerating columns are also used as the suppressor in the systems of the present invention.

The self-regeneration columns of applicants' co-pending applications are equipped with, inter alia, electrodes which permit electrolysis of the mobile phase. The electrolysis of the mobile phase provides a source of, for example, hydronium or hydroxide ions, which are flowed across the exhausted or partially exhausted ion-exchange bed of the self-regenerating column. These hydronium ions or hydroxide ions, as the case may be, convert the exhausted ion-exchange bed or resin back to either its hydronium or hydroxide form thereby regenerating the ion-exchange bed or resin of the column. In a preferred embodiment of the invention disclosed in applicants' co-pending applications, the suppressed detector effluent (which consists of deionized water) is the mobile phase which undergoes the electrolysis to yield the replenishing hydronium or hydroxide ions.

It occurred to applicants that the invention of its co-pending applications could be advantageously applied to the prior art problems associated with sample neutralization and pre-concentration outlined above. For further details concerning the preferred self-regeneration columns used in the systems and apparatus of this invention, those skilled in the art are encouraged to consult applicants' above-identified co-pending applications.

By using the self-regeneration columns of applicants' co-pending applications, the present invention overcomes some of the disadvantages of the prior art neutralization techniques. This is accomplished by using the electrochemically-regenerated ionexchange columns of applicants' co-pending applications to neutralize samples prior to IC analysis. By regenerating the ion-exchange bed between runs (or as often as necessary) as disclosed in applicants' co-pending applications, a single packed bed may be used to neutralize multiple samples, eliminating the cost of disposable cartridges that are typically used to process only one sample. An additional advantage to the system of the present invention is the inherently high ion-exchange capacity of ion-exchange beds. Thus, multiple neutralizations of samples may be accomplished without the recycling required with the prior art membrane-based devices, Additionally, the ion exchange beds of the present invention will tolerate the high backpressures typically encountered in HPLC and IC systems, and may be inserted in-line for greatly simplified operation compared to prior art micromembrane devices.

The system of this invention is also capable of automation using existing autosamplers such as the ALLTECH 580 Autosampler, eliminating labor-intensive manual off-line disposable packed-bed procedures. Finally, the present invention advantageously uses the suppressed detector effluent from the IC system to push the sample through the neutralization ion-exchange bed and to provide flow during electrochemical regeneration of the neutralization column or cartridge. This eliminates the need for a separate source of deionized water, as required by the prior art micromembrane devices.

A preferred aspect of the electrochemically regenerated ion neutralization system of the present invention will be described with reference to FIGS. 1, 2 and 3.

With reference to FIG. 1, the system preferably consists of an HPLC pump 1, a concentrator column 2, an analytical column 3, a suppressor 4, a conductivity detector 5, a mixed bed deionizing resin 6, a sample injection valve 7, a sample loop 8, neutralization ion exchange cartridge 9, and 10-port valve 10. The suppressor 4 preferably comprises two separate columns (not shown) as discussed in applicants' co-pending applications. Further details about the suppressor 4 are disclosed in applicants' co-pending applications.

Still with reference to FIG. 1, flow for sample loading is as follows. The detector effluent from the detector 5, which contains suppressed eluant and at times analytes from the previous run, is deionized by passing the detector effluent through mixed-bed deionizing resin 6. The effluent from the mixed-bed 6 (high-purity water) is flowed to a six-port manual or automated (autosampler) sample injection valve 7. The sample is loaded into a sample loop 8 in the sample injection valve 7. The mixed-bed effluent (high-purity water) is flowed through the sample injection valve 7 to the valve 10, and is delivered to the suppressor 4 through cartridge 9. At the suppressor 4, the water undergoes hydrolysis and electrochemically regenerates the suppressor 4 as described in applicants' co-pending applications. The electrolysis by-products from the regeneration of suppressor 4 is flowed to waste.

Still with reference to FIG. 1, mobile phase (the eluant) from the HPLC pump 1 is flowed through the valve 10, through concentrator 2, to the analytical column 3, to suppressor 4, and detector 5. The detector effuent is flowed through mixed-bed 6 to yield a steady supply of deionized water.

Figure 2:
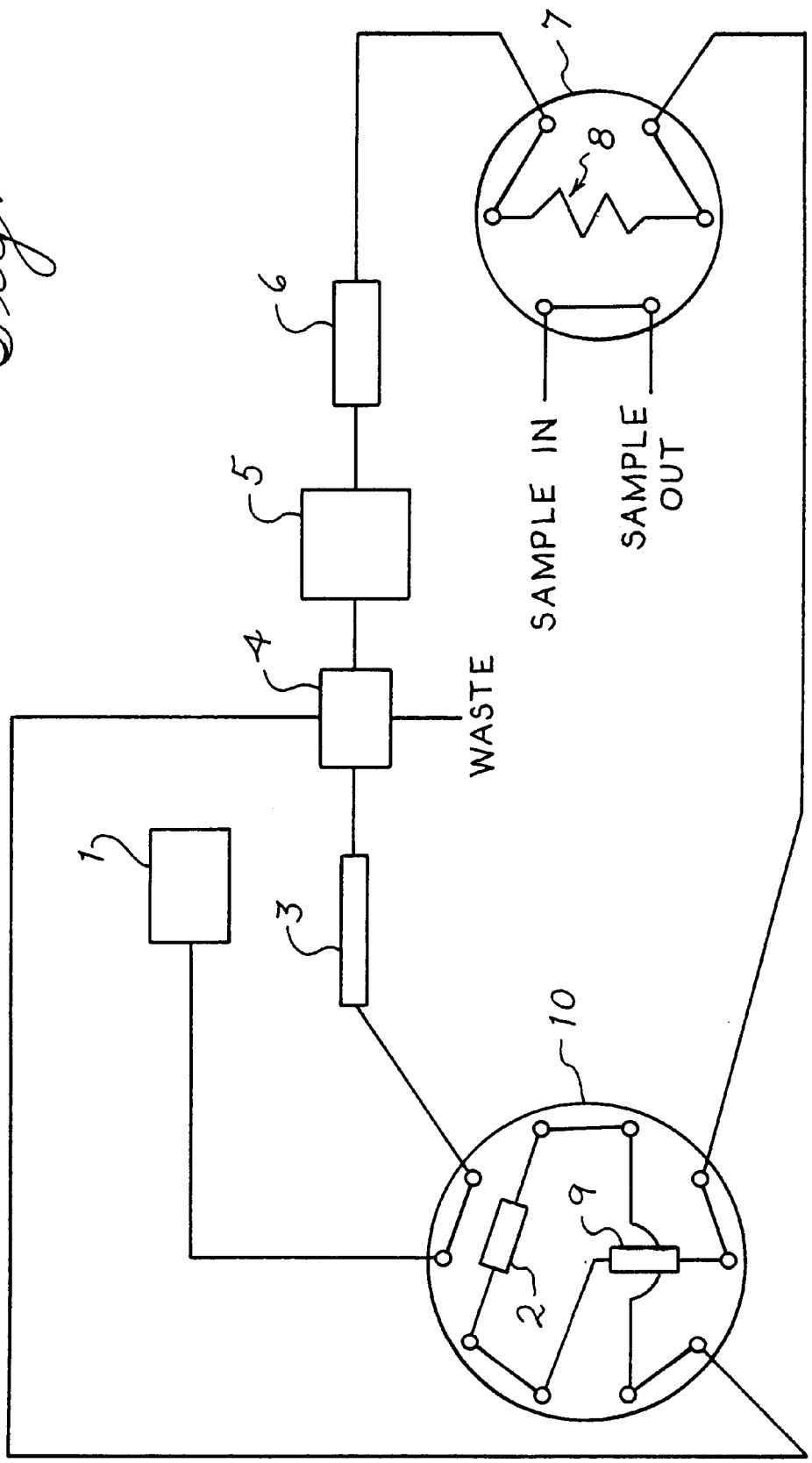
Fig. 2 is a schematic view of one aspect of the invention showing the system configuration for sample neutralization in electronically regenerated ion neutralization.

With reference to FIG. 2, for sample neutralization the mobile phase flow in both the sample injection valve 7 and the valve 10 is switched. The mixed-bed effluent (high purity water) is flowed from the mixed-bed 6 to the sample injection valve 7, and then flows or delivers the sample from sample loop 8 to valve 10. Still under the driving pressure from the mixed-bed effluent, the sample is flowed through the neutralization ion exchange cartridge 9. The cartridge preferably comprises a packed-bed neutralization ion-exchange resin. Here, the sample undergoes the previously described neutralization reactions. An anion exchange resin in the hydroxide form may be used for neutralization in cation analysis. A cation exchange resin bed in the hydronium form may be used for neutralization in anion analysis. The various cation and anion exchange resins disclosed in applicants' co-pending application are preferably used.

The effluent from the neutralization ion exchange cartridge 9, which contains the sample ions in high-purity water, is flowed to a concentrator column 2. The analyte or sample ions are retained by ion-exchange resin in the concentrator column 2. The concentrator column 2 is preferably a very small (4.6 mm×7.5 mm) bed filled with the same packing material used in the analytical column 3. The preferred resins for cation or anion analysis are disclosed in applicants' co-pending applications. In any event, because the sample ions are delivered to the concentrator column 2 by deionized water, which has little or no eluting power, the sample ions are retained on the concentrator column 2 without breakthrough. The mobile phase flow in sample injection valve 7 and valve 10 is maintained until all of the sample has been flowed through the neutralization bed 9 and to the concentrator column 2. The concentrator effluent, which is water, is flowed to the suppressor 4 for hydrolysis and regenerating an exhausted or partially exhausted suppressor column as described in applicants' co-pending applications. During this process, the mobile phase from HPLC pump 1 is flowed to the analytical column 3 through the valve 10. The analytical column effluent is flowed to the suppressor 4, where it is flowed through the on-line suppressor column in the suppressor. The sample ions and the suppressed mobile phase are then flowed to the detector 5 for sample ion detection and quantification.

Figure 3:
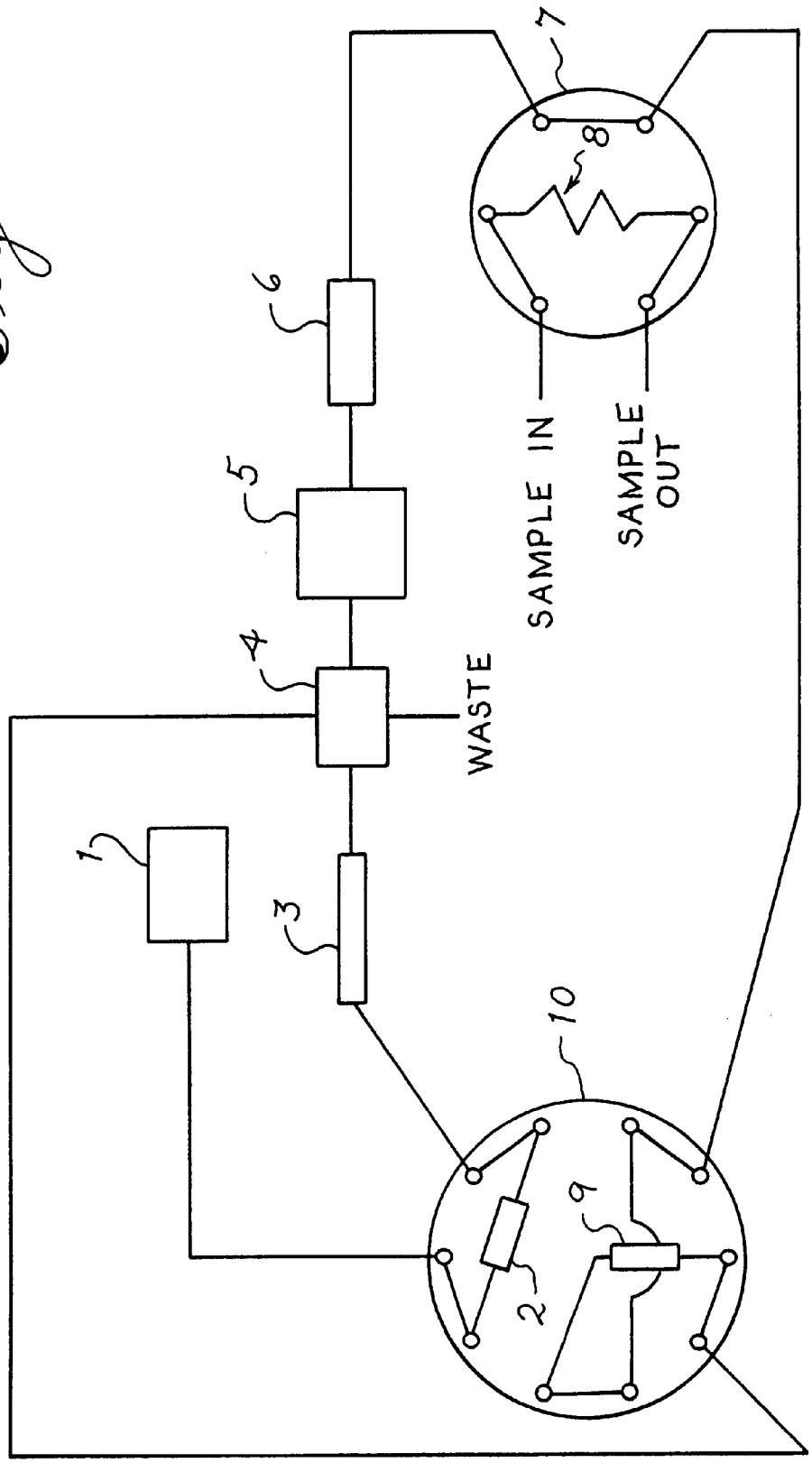
FIG. 3 is a schematic view of one aspect of the invention showing the system configuration for sample analysis in electronically regenerated ion neutralization.

With reference to FIG. 3, for sample analysis the mobile phase flow in both valves 10 and 7 is switched back to the flow depicted in sample loading (FIG. 1). The valve 10 flows mobile phase (eluant) from the HPLC pump 1 to the concentrator column 2. The mobile phase elutes the sample ions from the concentrator column 2, and flows the sample ions to the analytical column 3 for separation. The separated sample ions are then flowed to suppressor 4, where the mobile phase is suppressed. The suppressor 4 is constructed as previously described in applicants' co-pending applications. The suppressed mobile phase then flows the sample ions to detector 5 for detection and quantification.

The mobile phase from detector 5 (detector effluent), which contains sample ions, is then flowed to the mixed-bed deionization resin 6 where the sample ions are exchanged with hydronium or hydroxide ions, as the case may be to yield water. The mixed-bed is deionizing effluent (highly pure water) is flowed to the sample injection valve 7 and then to the valve 10. The neutralization ion exchange cartridge 9 is constructed like the self-regenerating columns disclosed in applicants' co-pending applications. The mobile phase (which is water at this point) is flowed to cartridge 9 and a power source (not disclosed) is activated to permit electrolysis of the mobile phase thereby electrochemically regenerating the exhausted or partially exhausted resin contained therein as described in applicants' co-pending applications. The regeneration current and regeneration time are adjusted to completely displace the retained sample counterions and purge electrolysis byproducts from the bed before the next sample is applied. The neutralization cartridge 9 effluent is flowed to suppressor 4, where it may be flowed to waste or used to regenerate an exhausted suppressor column in suppressor 4. During this time, the next sample to be loaded is flowed into the sample loop 8 of injection valve 7.

In all flow configurations, the waste from the valve 10 is continuously fed into the suppressor 4 as a feed source for electrochemically regenerating the suppressor 4 as disclosed in applicants' co-pending applications. If analysis time permits, however, it is preferred to sequentially regenerate cartridge 9 and then suppressor 4.

The foregoing system discussed with respect to FIGS. 1–3 can be reconfigured for use in electrochemically regenerated ion concentration. This can be accomplished by removing the neutralization ion-exchange cartridge 9 from the valve 10 shown in FIGS. 1–3. In this fashion, large volumes of dilute samples can be flowed from the sample loop 8 in the injection valve 7 onto the concentrator column 2 in the valve 10 without requiring a secondary pump. This involves a three step process, which will be described with reference to FIGS. 1–3.

Sample is loaded into the system in the same fashion as previously described with respect to FIG. 1.

With reference to FIG. 2, for sample concentration mobile phase flow is switched in sample injection valve 7 and valve 10 and mixed-bed 6 effluent (deionized water) is flowed to the sample injection valve 7 (preferably a six-port valve). The mixed-bed effluent then flows the sample from the sample loop 8 to the valve 10 (preferably a 10-port valve). The sample loop 8 preferably contains a large volume (1 mL to 100 mL) of sample to provide the desired preconcentration effect. Recall that in this embodiment there is not a neutralization ion exchange cartridge 9 connected to valve 10. The sample is flowed through a concentrator column 2 where sample ions are retained by ion-exchange. The concentrator column 2 preferably is a very small (4.6 mm×7.5 mm) bed filled with the same packing materials used in the analytical column 3. The preferred cation and anion exchange resins are disclosed in applicants' co-pending applications. Because the sample ions are delivered to the concentrator column 2 by deionized water, which has little or no eluting power, the sample ions are retained on the concentrator column 2 without breakthrough. The mobile phase flow in injection valve 7 and valve 10 continues until all of the sample has been delivered onto the concentrator 2. During this process, the HPLC pump 1 delivers mobile phase (eluant) to the analytical column 3 through the valve 10 and through suppressor 4. The suppressed eluant is flowed through the mixed bed 6 yielding a steady source of deionized water.

With reference to FIG. 3, for sample analysis mobile phase flow is switched in sample injection valve 7 and valve 10. The mobile phase flow through valve 10 is from the HPLC pump 1 to the concentrator column 2. The mobile phase elutes the sample ions from the concentrator column 2 and flows the sample ions to the analytical column 3 where the sample ions are separated. The mobile phase then flows the separated sample ions to suppressor 4 where the mobile phase is suppressed. The sample ions and the suppressed mobile phase is flowed to detector 5 where the sample ions are detected and quantified. During this time, the sample injection valve 7 is positioned to accept the next sample.

During all three steps, the waste from the valve 10 (deionized water) is continuously fed into the suppressor 4 as a feed source for electrochemically regenerating the suppressor as described in applicants' co-pending applications.

Many of the preferred materials for use in the present invention are disclosed ir applicants' co-pending application. Other preferred materials for ion neutralization include: for anions in caustic (NaOH) solution—analytical column—ALLTECH's ALLSEP Anionic Column, 100×4 mm; mobile phase—0.85 mM $NaHCO_3$:0.9 mM $Na_2CO_3$; flowrate—1.2 mL/min; detector-suppressed conductivity; for cations in HCl—analytical column—Universal Cation, 100×4.6 mm; mobile phase—3 mM Methanesulfonic Acid; flowrate—1.0 mL/min; column temperature—35° C.; dector—conductivity; for trace anions in silica HPLC stationary phase—column ALLSEP anionic column, 100×4.6 mm; mobile phase—0.85 mM $NaHCO_3$:0.9 mM $Na_2CO_3$; flowrate—1.2 mL/min detector-suppressed conductivity; for trace cations in nickel plating bath (35,000 ppm boric acid)-column—Universal Cation, 100×4.6; mobile phase—3 mM Methanesulfonic Acid; flowrate—1.0 mL/min; column temperature—35° C.; and detector-Conductivity. The various materials and apparatus described above and in applicants' co-pending application are available from the assignee of these applications, ALLTECH ASSOCIATES, INC., Deerfield, Ill.

As those skilled in the art will recognize, the systems and methods of the present invention can be used in variety of modified forms and applications. The foregoing discussion is intended to describe certain preferred aspects of the present invention and should not be considered to limit the scope of the invention.

What is claimed is:

1. A method of ion chromatography using mobile phase neutralization comprising:

(a) flowing a mobile phase comprising interfering ions and sample ions through a neutralizer ion exchange resin comprising neutralization ions selected from the group consisting of hydronium ions and hydroxide ions thereby at least partially exhausting the neutralizer ion exchange resin and generating a neutralizer effluent comprising the sample ions;

(b) flowing the neutralizer effluent to an analytical column and separating the sample ions;

(c) flowing the sample ions to a detector and detecting the sample ions; and (d) after the completion of step (a) applying an electrical potential through the at least partially exhausted neutralizer ion exchange resin while flowing an aqueous liquid stream therethrough to electrolyze water thereby regenerating the neutralizer ion exchange resin, the application of the electrical potential being discontinued during step (a).

2. The method of claim 1 wherein after step (c) a detector effluent comprising sample ions is flowed through a deionization resin to remove sample ions thereby forming a dionization resin effluent and using the deionization resin effluent as the aqueous liquid stream in step (d).

3. The method of claim 1 wherein prior to step (c) the separated sample ions are flowed through a suppressor.

4. The method of claim 1 wherein the neutralization ions comprise hydronium ions.

* * * * *